(12) United States Patent
Thiagrajan et al.

(10) Patent No.: US 8,942,800 B2
(45) Date of Patent: Jan. 27, 2015

(54) CORRECTIVE PROMPTING SYSTEM FOR APPROPRIATE CHEST COMPRESSIONS

(71) Applicant: Cardiac Science Corporation, Waukesha, WI (US)

(72) Inventors: Srikanth Thiagrajan, Tustin, CA (US); James Walter Taylor, Laguna Niguel, CA (US)

(73) Assignee: Cardiac Science Corporation, Waukesha, WI (US)

( * ) Notice: Subject to any disclaimer, the term of this patent is extended or adjusted under 35 U.S.C. 154(b) by 28 days.

(21) Appl. No.: 13/670,841

(22) Filed: Nov. 7, 2012

(65) Prior Publication Data
US 2013/0282069 A1   Oct. 24, 2013

Related U.S. Application Data

(60) Provisional application No. 61/636,419, filed on Apr. 20, 2012.

(51) Int. Cl.
*A61N 1/39* (2006.01)
*A61H 31/00* (2006.01)

(52) U.S. Cl.
CPC ............ *A61N 1/3993* (2013.01); *A61H 31/005* (2013.01); *A61H 31/007* (2013.01);
(Continued)

(58) Field of Classification Search
USPC ................................... 607/5–6; 600/587, 595
See application file for complete search history.

(56) References Cited

U.S. PATENT DOCUMENTS

| | | | |
|---|---|---|---|
| 4,202,340 A | 5/1980 | Langer et al. | |
| 4,231,365 A | 11/1980 | Scarberry | |

(Continued)

FOREIGN PATENT DOCUMENTS

| | | |
|---|---|---|
| EP | 1491176 | 12/2004 |
| EP | 1057451 B1 | 4/2009 |

(Continued)

OTHER PUBLICATIONS

G. Ristagno et al., "The quality of chest compressions during cardiopulmonary resuscitation overrides importance of timing of defibrillation", Chest, 132, 70-75, 2007. 6 Pgs.

(Continued)

*Primary Examiner* — Rex R Holmes
(74) *Attorney, Agent, or Firm* — Patterson Thuente Pedersen P.A.

(57) ABSTRACT

An automated external defibrillator (AED) and methods for a corrective CPR prompting system. The AED includes a sensor that obtains compression measurement data of CPR chest compressions and a control system including a microprocessor programmed to run a non-parametric, Information-Theoretic analysis of the compression measurement data. The analysis includes ranking provided compression measurement data, determining a prompt time $T_N$ for review, locating the compression measurement data at $T_N$ in an initial expected histogram of depth and rate aspects of the compression data measurements with upper and lower limits, that divides the intervals of the histogram into a plurality of sections, weighting the compression measurement data based on a plurality of factors, deriving information content of the compression measurement data by mapping a probability density function into an information content function, and determining if a particular corrective prompt is necessary. The AED also includes a prompting device that provides corrective CPR.

13 Claims, 13 Drawing Sheets

(52) U.S. Cl.
CPC . *A61H2201/0184* (2013.01); *A61H 2201/5007* (2013.01); *A61H 2201/5015* (2013.01); *A61H 2201/5043* (2013.01); *A61H 2201/5048* (2013.01); *A61H 2201/5061* (2013.01); *A61H 2201/5071* (2013.01); *A61H 2201/5084* (2013.01); *A61H 2201/5092* (2013.01); *A61H 2201/5097* (2013.01); *A61H 2230/04* (2013.01)
USPC .......................................................... 607/3

(56) References Cited

U.S. PATENT DOCUMENTS

| | | | |
|---|---|---|---|
| 4,338,924 A | 7/1982 | Bloom |
| 4,397,306 A | 8/1983 | Weisfeldt et al. |
| 4,481,938 A | 11/1984 | Lindley |
| 4,583,524 A | 4/1986 | Hutchins |
| 4,588,383 A | 5/1986 | Parker et al. |
| 4,610,254 A | 9/1986 | Morgan et al. |
| 4,611,998 A | 9/1986 | Ramamurthy |
| 4,619,617 A | 10/1986 | Rice |
| 4,770,165 A | 9/1988 | Hayek |
| 4,850,876 A | 7/1989 | Lutaenko et al. |
| 4,863,385 A | 9/1989 | Pierce |
| 4,915,095 A | 4/1990 | Chun |
| 4,926,844 A | 5/1990 | Lindley |
| 4,928,674 A | 5/1990 | Halperin et al. |
| 4,945,899 A | 8/1990 | Sugiyama et al. |
| 4,984,987 A | 1/1991 | Brault et al. |
| 5,195,896 A | 3/1993 | Sweeney et al. |
| 5,247,939 A | 9/1993 | Sjoquist et al. |
| 5,249,968 A | 10/1993 | Brault et al. |
| 5,256,070 A | 10/1993 | Garth et al. |
| 5,279,283 A | 1/1994 | Dillon |
| 5,286,206 A | 2/1994 | Epstein et al. |
| 5,295,481 A | 3/1994 | Geeham |
| 5,315,995 A | 5/1994 | Rivers |
| 5,330,514 A | 7/1994 | Egelandsdal et al. |
| RE34,800 E | 11/1994 | Hutchins |
| 5,370,603 A | 12/1994 | Newman |
| 5,394,892 A | 3/1995 | Kenny et al. |
| 5,413,558 A | 5/1995 | Paradis |
| 5,423,685 A | 6/1995 | Adamson et al. |
| 5,454,779 A | 10/1995 | Lurie et al. |
| 5,468,151 A | 11/1995 | Egelandsdal et al. |
| 5,474,574 A | 12/1995 | Payne et al. |
| 5,496,257 A | 3/1996 | Kelly |
| 5,551,420 A | 9/1996 | Lurie et al. |
| 5,589,639 A | 12/1996 | D'Antonio et al. |
| 5,593,306 A | 1/1997 | Kohnke |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,645,522 A | 7/1997 | Lurie et al. |
| 5,645,571 A | 7/1997 | Olson et al. |
| 5,652,897 A | 7/1997 | Linebarger et al. |
| 5,662,690 A | 9/1997 | Cole et al. |
| 5,692,498 A | 12/1997 | Lurie et al. |
| 5,735,879 A | 4/1998 | Gliner et al. |
| 5,749,902 A | 5/1998 | Olson et al. |
| 5,749,904 A | 5/1998 | Gliner et al. |
| 5,749,905 A | 5/1998 | Gliner et al. |
| 5,769,800 A | 6/1998 | Gelfand et al. |
| 5,772,613 A | 6/1998 | Gelfand et al. |
| 5,792,190 A | 8/1998 | Olson et al. |
| 5,792,204 A | 8/1998 | Snell |
| 5,797,969 A | 8/1998 | Olson et al. |
| D399,000 S | 9/1998 | Rothman et al. |
| 5,803,927 A | 9/1998 | Cameron et al. |
| 5,885,084 A | 3/1999 | Pastrick et al. |
| D411,620 S | 6/1999 | Lindseth et al. |
| 5,913,685 A | 6/1999 | Hutchins |
| 5,917,484 A | 6/1999 | Mullaney |
| 5,919,212 A | 7/1999 | Olson et al. |
| 5,927,273 A | 7/1999 | Federowicz et al. |
| 5,931,850 A | 8/1999 | Zadini et al. |
| 5,951,598 A | 9/1999 | Bishay et al. |
| 5,957,856 A | 9/1999 | Weil et al. |
| D415,200 S | 10/1999 | Carpenter et al. |
| D417,702 S | 12/1999 | Carpenter et al. |
| 5,997,488 A | 12/1999 | Gelfand et al. |
| 5,999,493 A | 12/1999 | Olson |
| 6,062,219 A | 5/2000 | Lurie et al. |
| 6,066,106 A | 5/2000 | Sherman et al. |
| 6,083,246 A | 7/2000 | Stendahl et al. |
| 6,088,617 A | 7/2000 | Arand et al. |
| D429,500 S | 8/2000 | Brault et al. |
| 6,125,299 A | 9/2000 | Groenke et al. |
| 6,154,673 A | 11/2000 | Morgan et al. |
| 6,155,257 A | 12/2000 | Lurie et al. |
| 6,171,257 B1 | 1/2001 | Weil et al. |
| 6,174,295 B1 | 1/2001 | Cantrell et al. |
| 6,193,519 B1 | 2/2001 | Eggert et al. |
| 6,201,992 B1 | 3/2001 | Freeman |
| 6,204,885 B1 | 3/2001 | Kwoh |
| 6,224,562 B1 | 5/2001 | Lurie et al. |
| 6,234,985 B1 | 5/2001 | Lurie et al. |
| 6,240,170 B1 | 5/2001 | Shaffer et al. |
| 6,246,907 B1 | 6/2001 | Lin et al. |
| 6,289,243 B1 | 9/2001 | Lin et al. |
| 6,306,107 B1 | 10/2001 | Myklebust et al. |
| 6,312,399 B1 | 11/2001 | Lurie et al. |
| 6,314,320 B1 | 11/2001 | Powers et al. |
| 6,327,497 B1 | 12/2001 | Kirchgeorg et al. |
| 6,334,070 B1 | 12/2001 | Nova et al. |
| 6,336,047 B1 | 1/2002 | Thu et al. |
| 6,351,671 B1 | 2/2002 | Myklebust et al. |
| 6,356,785 B1 | 3/2002 | Snyder et al. |
| 6,360,120 B1 | 3/2002 | Powers et al. |
| 6,360,602 B1 | 3/2002 | Tazartes et al. |
| 6,374,827 B1 | 4/2002 | Bowden et al. |
| 6,390,996 B1 | 5/2002 | Halperin et al. |
| 6,398,745 B1 | 6/2002 | Sherman et al. |
| 6,438,415 B1 | 8/2002 | Powers |
| 6,447,465 B1 | 9/2002 | Sherman et al. |
| 6,463,327 B1 | 10/2002 | Lurie et al. |
| D466,215 S | 11/2002 | Lindseth et al. |
| 6,500,009 B1 | 12/2002 | Brault et al. |
| 6,526,973 B1 | 3/2003 | Lurie et al. |
| 6,546,813 B2 | 4/2003 | Hubbard |
| 6,604,523 B2 | 8/2003 | Lurie et al. |
| 6,611,708 B1 | 8/2003 | Morgan et al. |
| 6,616,620 B2 | 9/2003 | Sherman et al. |
| 6,648,841 B1 | 11/2003 | Sessler |
| 6,658,290 B1 | 12/2003 | Lin et al. |
| D485,360 S | 1/2004 | Faller et al. |
| 6,676,613 B2 | 1/2004 | Cantrell et al. |
| 6,694,299 B1 | 2/2004 | Barrer |
| 6,697,671 B1 | 2/2004 | Nova et al. |
| 6,709,410 B2 | 3/2004 | Sherman et al. |
| RE38,533 E | 6/2004 | Kirchgeorg et al. |
| 6,754,526 B2 | 6/2004 | Daynes et al. |
| 6,758,676 B2 | 7/2004 | Eggert et al. |
| 6,780,017 B2 | 8/2004 | Pastrick et al. |
| 6,789,540 B1 | 9/2004 | Lin |
| 6,792,947 B1 | 9/2004 | Bowden |
| 6,807,442 B1 | 10/2004 | Myklebust et al. |
| D499,183 S | 11/2004 | Vaisnys et al. |
| 6,827,695 B2 | 12/2004 | Palazzolo et al. |
| 6,865,413 B2 | 3/2005 | Halperin et al. |
| 6,869,408 B2 | 3/2005 | Sherman et al. |
| 6,869,409 B2 | 3/2005 | Rothman et al. |
| 6,872,080 B2 | 3/2005 | Pastrick et al. |
| 6,920,354 B2 | 7/2005 | Daynes et al. |
| 6,961,612 B2 | 11/2005 | Elghazzawi et al. |
| 6,969,259 B2 | 11/2005 | Pastrick et al. |
| 6,993,386 B2 | 1/2006 | Lin et al. |
| 7,056,295 B2 | 6/2006 | Halperin |
| 7,069,074 B2 | 6/2006 | Covey et al. |
| 7,074,199 B2 | 7/2006 | Halperin et al. |
| 7,108,665 B2 | 9/2006 | Halperin et al. |
| 7,114,954 B2 | 10/2006 | Eggert et al. |
| 7,118,542 B2 | 10/2006 | Palazzolo et al. |
| 7,122,014 B2 | 10/2006 | Palazzolo et al. |

(56) References Cited

U.S. PATENT DOCUMENTS

| | | |
|---|---|---|
| 7,131,953 B2 | 11/2006 | Sherman et al. |
| 7,164,945 B2 | 1/2007 | Hamilton et al. |
| 7,166,082 B2 | 1/2007 | Sherman et al. |
| 7,174,891 B2 | 2/2007 | Lurie et al. |
| 7,190,999 B2 | 3/2007 | Geheb et al. |
| 7,192,284 B2 | 3/2007 | Eggert et al. |
| 7,210,480 B2 | 5/2007 | Lurie et al. |
| 7,211,056 B2 | 5/2007 | Petelenz et al. |
| 7,220,235 B2 | 5/2007 | Geheb et al. |
| 7,226,427 B2 | 6/2007 | Steen |
| 7,231,249 B2 | 6/2007 | Mower |
| 7,245,974 B2 | 7/2007 | Dupelle et al. |
| 7,257,440 B2 | 8/2007 | Morgan et al. |
| 7,259,667 B2 | 8/2007 | Sergio et al. |
| RE39,897 E | 10/2007 | Mower |
| 7,295,871 B2 | 11/2007 | Halperin et al. |
| 7,310,553 B2 | 12/2007 | Freeman |
| 7,359,749 B2 | 4/2008 | Quenet et al. |
| 7,374,548 B2 | 5/2008 | Sherman et al. |
| RE40,365 E | 6/2008 | Kirchgeorg et al. |
| 7,429,250 B2 | 9/2008 | Halperin et al. |
| 7,476,206 B2 | 1/2009 | Palazzolo et al. |
| 7,488,293 B2 | 2/2009 | Marcovecchio et al. |
| 7,497,837 B2 | 3/2009 | Sherman et al. |
| 7,517,325 B2 | 4/2009 | Halperin |
| 7,517,326 B2 | 4/2009 | Mollenauer et al. |
| 7,567,837 B2 | 7/2009 | Weil et al. |
| 7,569,021 B2 | 8/2009 | Sebelius et al. |
| 7,570,993 B2 | 8/2009 | Weil et al. |
| 7,623,915 B2 | 11/2009 | Sullivan et al. |
| 7,630,762 B2 | 12/2009 | Sullivan et al. |
| 7,645,247 B2 | 1/2010 | Paradis |
| 7,650,181 B2 | 1/2010 | Freeman et al. |
| 7,653,435 B2 | 1/2010 | Halsne |
| D609,813 S | 2/2010 | Molden et al. |
| D610,687 S | 2/2010 | Boggs et al. |
| 7,666,153 B2 | 2/2010 | Hall et al. |
| 7,666,154 B2 | 2/2010 | Bystrom et al. |
| 7,706,878 B2 | 4/2010 | Freeman |
| 7,715,913 B1 | 5/2010 | Froman et al. |
| 7,720,535 B2 | 5/2010 | Ni et al. |
| 7,722,554 B2 | 5/2010 | Sherman et al. |
| 7,729,757 B2 | 6/2010 | Parascandola et al. |
| 7,734,344 B2 | 6/2010 | Ideker et al. |
| 7,747,319 B2 | 6/2010 | Freeman |
| 7,766,011 B2 | 8/2010 | Lurie |
| 7,774,060 B2 | 8/2010 | Westenskow et al. |
| 7,775,996 B2 | 8/2010 | Strømsnes |
| 7,792,577 B2 | 9/2010 | Hamilton et al. |
| 7,797,044 B2 | 9/2010 | Covey et al. |
| 7,805,191 B2 | 9/2010 | Walker et al. |
| 7,811,090 B2 | 10/2010 | Eggert et al. |
| 7,818,049 B2 | 10/2010 | Halperin et al. |
| 7,822,471 B2 | 10/2010 | Bowers |
| 7,836,881 B2 | 11/2010 | Lurie et al. |
| 7,837,636 B2 | 11/2010 | Tjølsen et al. |
| 7,846,112 B2 | 12/2010 | Escudero et al. |
| 7,857,625 B2 | 12/2010 | Gomo |
| 7,909,784 B2 | 3/2011 | Kornaker |
| 7,917,209 B2 | 3/2011 | Joo et al. |
| 7,938,115 B2 | 5/2011 | Thompson et al. |
| 7,955,283 B2 | 6/2011 | Katz et al. |
| 7,970,464 B2 | 6/2011 | Walker et al. |
| 7,976,312 B2 | 7/2011 | Eggert et al. |
| 7,976,313 B2 | 7/2011 | Eggert et al. |
| 7,993,290 B2 | 8/2011 | Lund et al. |
| 7,996,081 B2 | 8/2011 | Bystrom et al. |
| 8,000,787 B2 | 8/2011 | Hamilton et al. |
| 8,002,720 B2 | 8/2011 | Hansen et al. |
| 8,007,451 B2 | 8/2011 | Håvardsholm et al. |
| 8,010,190 B2 | 8/2011 | Olson et al. |
| 8,016,598 B2 | 9/2011 | Eggert et al. |
| 8,034,006 B2 | 10/2011 | Celik-Butler et al. |
| 8,060,199 B2 | 11/2011 | Walker et al. |
| 8,062,239 B2 | 11/2011 | Sherman et al. |
| 8,096,962 B2 | 1/2012 | Palazzolo et al. |
| 8,105,249 B2 | 1/2012 | Freeman |
| 8,114,035 B2 | 2/2012 | Quintana et al. |
| 8,121,681 B2 | 2/2012 | Hampton et al. |
| 2004/0082888 A1 | 4/2004 | Palazzolo et al. |
| 2004/0267324 A1 | 12/2004 | Geheb et al. |
| 2005/0119706 A1 | 6/2005 | Ideker et al. |
| 2006/0019229 A1 | 1/2006 | Morallee et al. |
| 2006/0129191 A1 | 6/2006 | Sullivan et al. |
| 2007/0049976 A1 | 3/2007 | Ni et al. |
| 2007/0060785 A1 | 3/2007 | Freeman et al. |
| 2007/0276300 A1 | 11/2007 | Olson et al. |
| 2008/0146973 A1 | 6/2008 | Lund et al. |
| 2008/0300518 A1 | 12/2008 | Bowes |
| 2009/0240295 A1 | 9/2009 | Kellum |
| 2010/0004710 A1 | 1/2010 | Kellum |
| 2010/0022886 A1 | 1/2010 | Ayati et al. |
| 2010/0022904 A1 | 1/2010 | Centen |
| 2010/0049266 A1 | 2/2010 | Ochs et al. |
| 2010/0152800 A1 | 6/2010 | Walker et al. |
| 2010/0168809 A1 | 7/2010 | Freeman |
| 2010/0204623 A1 | 8/2010 | Ideker et al. |
| 2010/0211127 A1 | 8/2010 | Eerden |
| 2010/0221690 A1 | 9/2010 | Freeman et al. |
| 2010/0221691 A1 | 9/2010 | Freeman et al. |
| 2010/0222681 A1 | 9/2010 | Freeman et al. |
| 2010/0222717 A1 | 9/2010 | Freeman et al. |
| 2010/0222718 A1 | 9/2010 | Freeman et al. |
| 2010/0234908 A1 | 9/2010 | Didon |
| 2010/0234910 A1 | 9/2010 | Parascandola et al. |
| 2010/0312153 A1 | 12/2010 | McIntyre et al. |
| 2011/0040217 A1 | 2/2011 | Centen |
| 2011/0066089 A1 | 3/2011 | Udassi et al. |
| 2011/0082379 A1 | 4/2011 | Sullivan |
| 2011/0105930 A1 | 5/2011 | Thiagarajan et al. |
| 2011/0144708 A1 | 6/2011 | Joo et al. |
| 2012/0010543 A1 | 1/2012 | Johnson et al. |
| 2014/0100433 A1* | 4/2014 | Elghazzawi et al. .......... 600/301 |

FOREIGN PATENT DOCUMENTS

| | | |
|---|---|---|
| GB | 1538522 A | 1/1979 |
| WO | WO2005/021089 A1 | 3/2005 |
| WO | WO2006/088373 A1 | 8/2006 |
| WO | WO2010/009531 A1 | 1/2010 |
| WO | WO2010/096396 A1 | 8/2010 |
| WO | WO2010/099593 A1 | 9/2010 |
| WO | WO2010/099628 A1 | 9/2010 |
| WO | WO2012-001541 | 1/2012 |

OTHER PUBLICATIONS

R.A. Berg et al., "Immediate post-shock chest compressions improve outcome from prolonged ventricular fibrillation", *Resuscitation*, 78, 71-76, 2008. 12 Pgs.

B. Abella et al., "Quality of Cardiopulmonary Resuscitation During In-Hospital Cardiac Arrest", *JAMA*, 293, 305-310, 2005. 6 Pgs.

J. Yeung et al., "The use of CPR feedback/prompt devices during training and CPR performance: A systematic review", *Resuscitation*, 80, 743-751, 2009. 9 Pgs.

A.J. Handley et al., "Improving CPR performance using an audible feedback system suitable for incorporation into an automated external defibrillator", *Resuscitation*, 57, 57-62, Apr. 2003. 6 Pgs.

B.H. Roth et al., "Guardian: A Prototype Intelligent Agent for Intensive-Care Monitoring", *AAAI-94 Proceedings*, 1503, 1994. 1 Pg.

R. Schoenberg et al., "Making ICU Alarms Meaningful: a comparison of traditional vs. trend-based algorithms", *Proceedings of AMIA*, 1999, 379-383. 5 Pgs.

W. Zong et al., "Reduction of false arterial blood pressure alarms using signal quality assessment and relationships between the electrocardiogram and arterial blood pressure", *Med. Biol. Eng. Comput.*, 2004, 42, 698-706. 9 Pgs.

P.A. Lichter et al., "System to improve AED resuscitation using interactive CPR coaching", *Engineering in Medicine and Biology Society, 2009*. EMBC 2009. Annual International Conference of the IEEE, 6755-6760, 2009. 6 Pgs.

Geisser et al., *Modes of Parametric Statistical Inference*, John Wiley & Sons (2006), Chapters 1-4, 54 Pgs.

(56) References Cited

OTHER PUBLICATIONS

D.R. Cox, *Principles of Statistical Inference*, Cambridge University Press (2006), Chapters 1-4, 76 Pgs.

International Search Report and Written Opinion for International Application No. PCT/US2013/023567 dated May 15, 2013.
Extended EP Search Report Cited in EP Application No. 13152753.3, Dated Aug. 1, 2013, 8 Pgs.

* cited by examiner

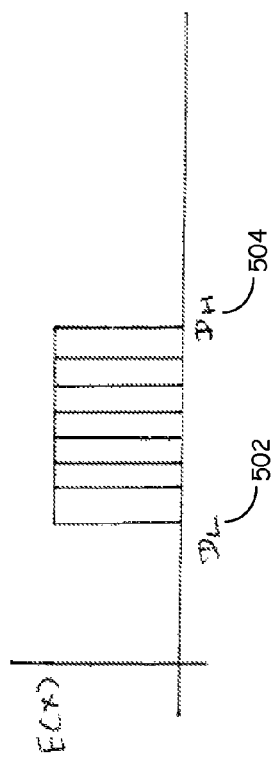
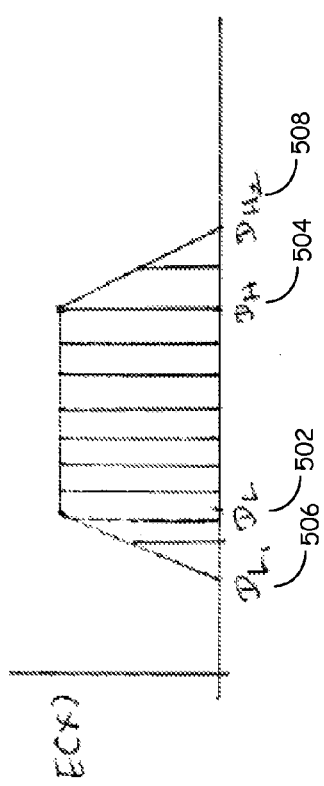
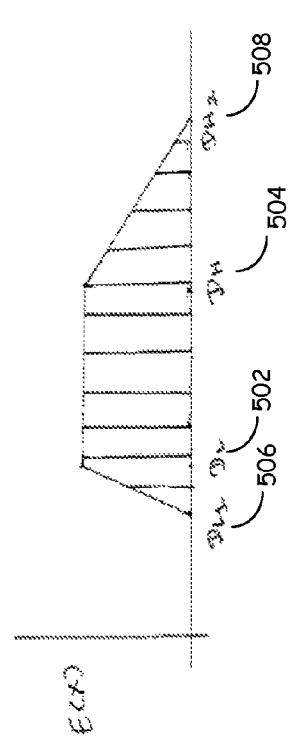
FIG. 5A
FIG. 5B
FIG. 5C

CORRECTIVE PROMPTING SYSTEM FOR APPROPRIATE CHEST COMPRESSIONS

RELATED APPLICATION

The present application claims the benefit of U.S. Provisional Application No. 61/636,419 filed Apr. 20, 2012, which is incorporated herein in its entirety by reference.

FIELD OF THE INVENTION

The present invention relates to improved methods and apparatus to assist users in administering cardio-pulmonary resuscitation (CPR) on cardiac arrest victims. Specifically, this invention relates to improved prompting systems for AEDs (Automated External Defibrillators), medical resuscitation devices, and associated methods that utilize sensor data regarding CPR performance to provide timely, accurate, and clear corrective instructions to individuals engaged in cardiac resuscitation.

BACKGROUND OF THE INVENTION

AEDs are well-known and widely used today to aid in both defibrillation and CPR. AEDs were developed decades ago to provide emergency therapy options during rescue situations for patients under cardiac arrest conditions. AEDs have become prevalent in public locales such as offices, shopping centers, stadiums, and other areas of high pedestrian traffic. AEDs empower citizens to provide medical help during cardiac emergencies in public places where such help was previously unavailable in the crucial early stages of a cardiac event.

Recent clinical guidelines emphasize the importance of good quality cardio-pulmonary resuscitation to maintain circulation in unconscious patients and to improve the odds of survival with an electrical shock. Because most cardiac arrests happen outside hospitals and in public places, devices like AEDs, which can assist CPR-trained members of the general public to perform better compressions, are of immense value to the community. Presently, some AEDs provide interfaces to sensors measuring the depth of compressions, rates of compressions, and effectiveness of compressions, including but not limited to piezoelectric sensors, pressure sensors, accelerometers, force sensors, and the like. However, in many devices, these measurements are not particularly useful as the measurements do not prove to provide effective instructions to the rescuer.

Therefore, improved methods and apparatus for rapidly assessing whether CPR is being effectively administered and quickly delivering appropriate corrective prompts to a rescuer are desired.

SUMMARY OF THE INVENTION

Various embodiments of the present invention overcome the problems of the prior art by providing a method and device for corrective prompting during CPR using Information-Theoretic criterion in which data from various sensors is processed during CPR for generating corrective prompts and a flexible and adaptive user interface is provided to controlling prompting. Embodiments of the present invention include an analysis of CPR compression history such that consistent and effective corrective prompts can be administered. Further, such embodiments recognize critical errors in compression that need immediate correction from mere minor errors and differentiation. A more advanced user interface and a plurality of CPR prompting choices are disclosed as well.

One embodiment is directed to an AED having a corrective CPR prompting system. The AED includes a sensor that obtains compression measurement data of CPR chest compressions. The AED further includes a control system including a microprocessor programmed to automatically run a non-parametric, Information-Theoretic analysis of the compression measurement data and store results in a memory assessment within the control system. The analysis includes ranking compression measurement data, determining a prompt time, creating a histogram of depth and rate measurements at the prompt time that divides intervals of the histogram into a plurality of sections, weighting the compression measurement data based on a plurality of factors, deriving information content of the compression measurement data by mapping a probability density function into an information content function, determining if a particular corrective prompt is necessary, and using a prompting device in the AED that provides corrective CPR instructions if corrective prompts are determined to be necessary.

Another embodiment of the present invention is directed to an AED having a corrective CPR prompting system. The AED includes a plurality of sensors, a control system, a prompting module and an adaptive user interface. The plurality of sensors obtain compression measurement data of CPR chest compressions and ECG data. The control system has a means for analyzing a history of the compression measurement data using a non-parametric Information-Theoretic criterion of the compression measurement data and determining if corrective prompts are necessary. The prompting module provides corrective CPR instructions if corrective prompts are determined to be necessary by the control system.

According to an embodiment of the present invention, a method for corrective CPR prompting with an AED using Information-Theoretic criterion is provided. The method includes sensing compression measurement data regarding chest compressions performed on a cardiac arrest victim using one or more sensors coupled with the AED. The method also includes ranking compression measurement data as it is received by the AED, determining a prompt time using a control system of the AED including a microprocessor, creating a histogram of depth and rate measurements at the prompt time with the control system, weighting data based on a plurality of factors with the control system, comparing the distribution of depth parameter data with an expected and acceptable distribution using the AED, and issuing corrective prompts for compressions of improper depth or improper speed.

BRIEF DESCRIPTION OF THE DRAWINGS

The invention may be more completely understood in consideration of the following detailed description of various embodiments of the invention in connection with the accompanying drawings, in which:

FIGS. 5A-C illustrate generally samples of potential histogram variations for lower depth thresholds and higher depth thresholds, according to an embodiment of the invention.

DETAILED DESCRIPTION OF THE PREFERRED EMBODIMENTS

The various embodiments of the invention may be embodied in other specific forms without departing from the essential attributes thereof, therefore, the illustrated embodiments should be considered in all respects as illustrative and not restrictive.

Figure 1A:
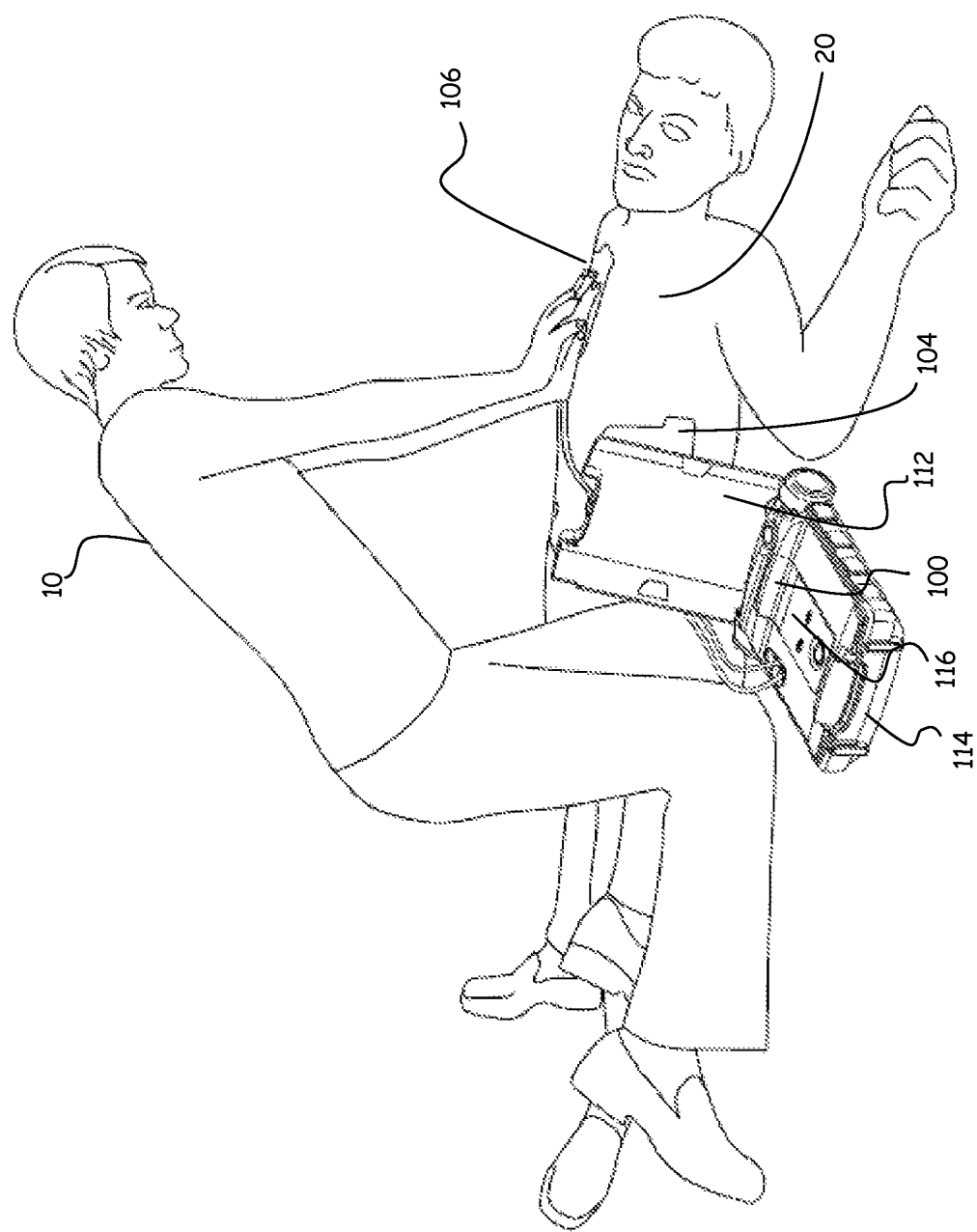
FIG. 1A illustrates generally an example of a cardiac arrest victim being treated with CPR and an AED, according to an embodiment of the invention.

In various embodiments of this invention an apparatus and method are disclosed for rapidly and reliably evaluating sensor compression data from a patient and issuing appropriate corrective prompting instructions. FIG. 1A depicts a cardiac arrest victim who is undergoing a resuscitation attempt and is being treated with CPR. The rescuer 10 is shown in position for rapidly providing chest compressions to the patient 20. The AHA has recommended that all rescuers, regardless of training, should provide chest compressions to all cardiac arrest victims, and that chest compressions should be the initial CPR action for all victims regardless of age. CPR typically improves a victim's chance of survival by providing critical blood circulation in the heart and brain.

Many current AEDS are equipped to assist with CPR by providing verbal and/or visual prompts to the rescuer. In FIG. 1A, the AED 100 is shown coupled to a pair of electrodes 104 and 106 located on the patient's chest. A further centrally located CPR assist device 108 (sometimes referred to as a "CPR puck") could be used with an AED in a resuscitation attempt as well. In some embodiments, the AED 100 is equipped with a central compartment having a hinged lid 112 that may house the electrode pads 104 and 106 and CPR assist device 108 when the AED 100 is not in use. The lid 112 is shown in an open configuration in FIG. 1A and accordingly, is ready for use. In one embodiment, opening this lid 112 activates the AED 100 and begins sending prompts to the user. Prompts may include voice prompts from speaker 114 and visual prompts from the display 116. Other embodiments may use other approaches for actuating the AED, such as buttons or voice recognition and prompts.

Figure 1B:
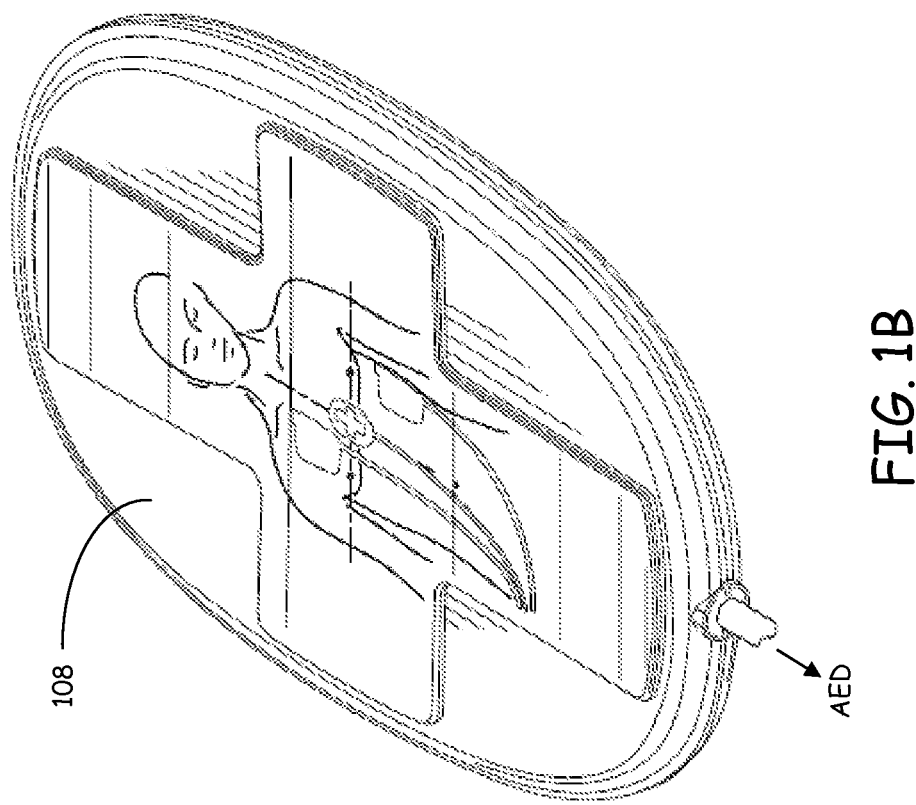
FIG. 1B illustrates an example of a CPR assist device for an AED, according to an embodiment of the invention.
Figure 1C:
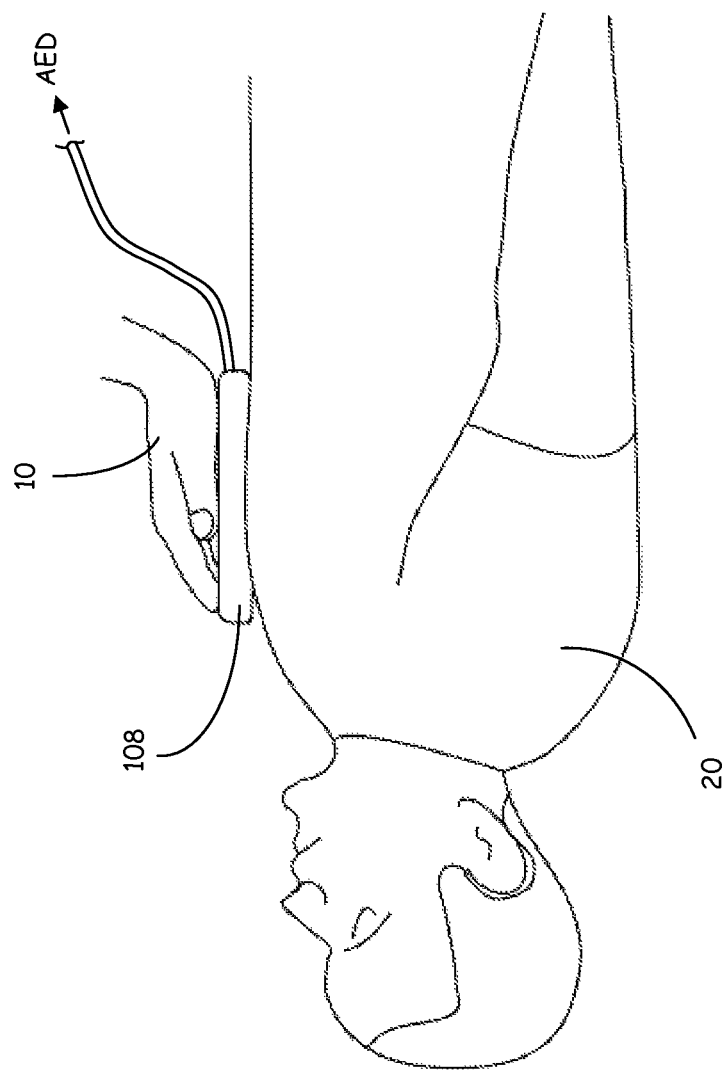
FIG. 1C illustrates an example of a CPR assist device for an AED being used on a cardiac arrest victim, according to an embodiment of the invention.

Various sensors may be used to make measurements with respect to CPR performance as part of the AED. These sensors may be incorporated into a CPR assist device 108 or be implemented as part of the some other CPR device or sensor. Examples of sensors that could be used include pressure sensors, force sensors, accelerometers, piezoelectric sensors, ultrasonic sensors, optical sensors, and others. FIGS. 1B and 1C depict examples of CPR assist devices 108 that can be used by a rescuer 10 on a cardiac arrest victim 20. Sensors may be implemented as part of the cardiac assist device 108 as part of an attachment to the AED as part of a separate device that communicates with the AED or as part of the AED itself.

Figure 2:
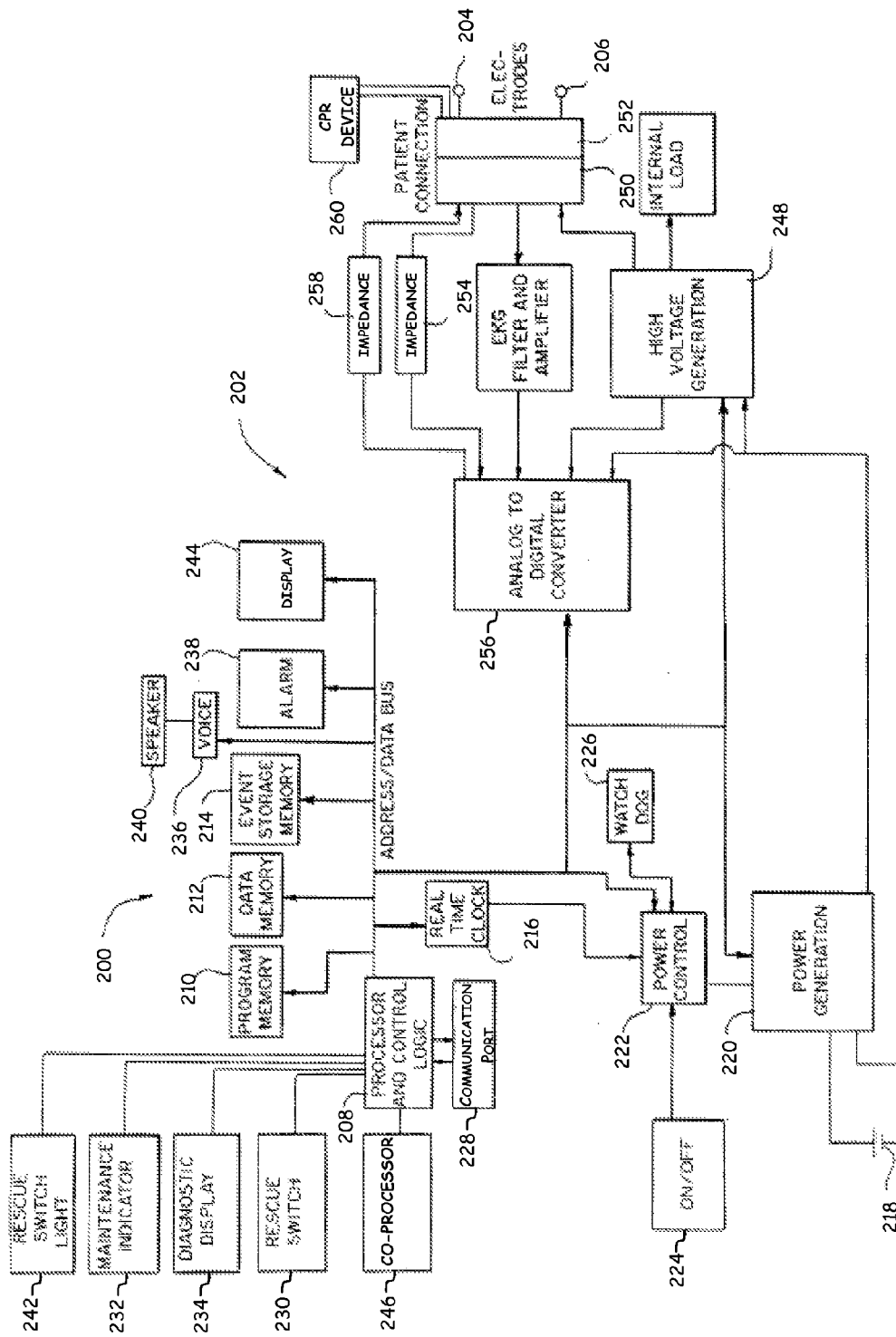
FIG. 2 illustrates generally an example of a schematic drawing of the hardware of an AED, according to an embodiment of the invention.

FIG. 2 illustrates a general block diagram of the components of an AED 200 implementing the improved CPR prompting system disclosed according to one embodiment of the invention. A digital microprocessor-based control system 202 is used for controlling the overall operation of AED 200. The electrical control system 202 further includes an impedance measuring circuit for testing the interconnection and operability of electrodes 204 and 206. Control system 202 includes a processor 208 interfaced to program memory 210, data memory 212, event memory 214 and real time clock 216. The operating program executed by processor 208 is stored in program memory 210. Electrical power is provided by the battery 218 and is connected to power generation circuit 220.

Power generation circuit 220 is also connected to power control unit 222, lid switch 224, watch dog timer 226, real time clock 216 and processor 208. A data communication port 228 is coupled to processor 208 for data transfer. In certain embodiments, the data transfer may be performed utilizing a serial port, USB port, Firewire, wireless such as 802.11X or 3G, radio and the like. Rescue switch 230, maintenance indicator 232, diagnostic display panel 234, the voice circuit 236 and audible alarm 238 are also connected to processor 208. Voice circuit 236 is connected to speaker 240. In various embodiments, rescue light switch 242 and a visual display 244 is connected to the processor 208 to provide additional operation information.

In certain embodiments, the AED will have a processor 208 and a co-processor 246. The co-processor 246 may be the CPR prompting algorithm implemented in hardware and operably connected to the processor over a high-speed data bus. In various embodiments, the processor 218 and co-processor 246 are on the same silicon and may be implemented in a multi-core processor. Alternatively, the processor 208 and co-processor may be implemented as part of a multi-processor or even networked processor arrangement. In these embodiments, the processor 208 offloads some of the calculations to the co-processor thus optimizing the processing of the sensed signals from the electrodes 204 and 206. In other embodiments, the processor 208 is optimized with specific instructions or optimizations to execute calculations. Thus, processor 210 may execute calculations in fewer clock cycles and while commanding fewer hardware resources. In other embodiments, the logic and algorithm of the control system 202 may be implemented in logic, either hardware in the form of an ASIC or a combination in the form of an FPGA, or the like.

High voltage generation circuit 248 is also connected to and controlled by processor 208. High voltage generation circuit 248 may contain semiconductor switches (not shown) and a plurality of capacitors (not shown). In various embodiments, connectors 250, 252 link the high voltage generation circuit 248 to electrodes 204 and 206. The high voltage circuit here is battery powered and is of high power.

Impedance measuring circuit 254 is connected to both connector 250 and real time clock 216. Impedance measuring circuit 254 is interfaced to real time clock through analog-to-digital (A/D) converter 256. Another impedance measuring circuit 258 may be connected to connector 250 and real time clock 216 and interfaced to processor 208 through analog-to-digital (A/D) converter 256. A CPR device 260 may optionally be connected to the processor 208 and real time clock 216 through connector 252 and A/D converter 256. The CPR device 260 may be a chest compression detection device or a manual, automatic, or semi-automatic mechanical chest compression device. In some embodiments the CPR device will correspond to a CPR puck like the CPR assist device 108 previously mentioned. Additional detailed discussions of some AED designs can be found in U.S. Pat. Pub. No. 2011/0105930 and U.S. Pat. Nos. 5,474,574, 5,645,571, 5,749,902, 5,792,190, 5,797,969, 5,919,212, 5,999,493, 6,083,246, 6,246,907, 6,289,243, 6,658,290, 6,993,386, each of which is hereby incorporated by reference.

AEDs with prompting capabilities as well as CPR assist devices have been known for some time, however, applicants have recognized a number of deficiencies in prompting devices of the past. For example, some past systems have difficulty supporting multiple filters and decision making systems when applied to real-time signals and can be computationally expensive to support. Moreover, many past systems cannot reliably detect and appropriately respond to fast-changing situations.

It should be noted that, to remain effective, prompts must be chosen strategically and be directed to critical aspects of the response. Further, prompts must be timely and be associated with recognizable actions by the rescuer. Moreover, prompts should be varied and identifiable despite potential confusion of the rescuer. Prompts should also be terse and timed to provide quiet times to respond to the prompt and avoid overwhelming the rescuer.

Figure 3:
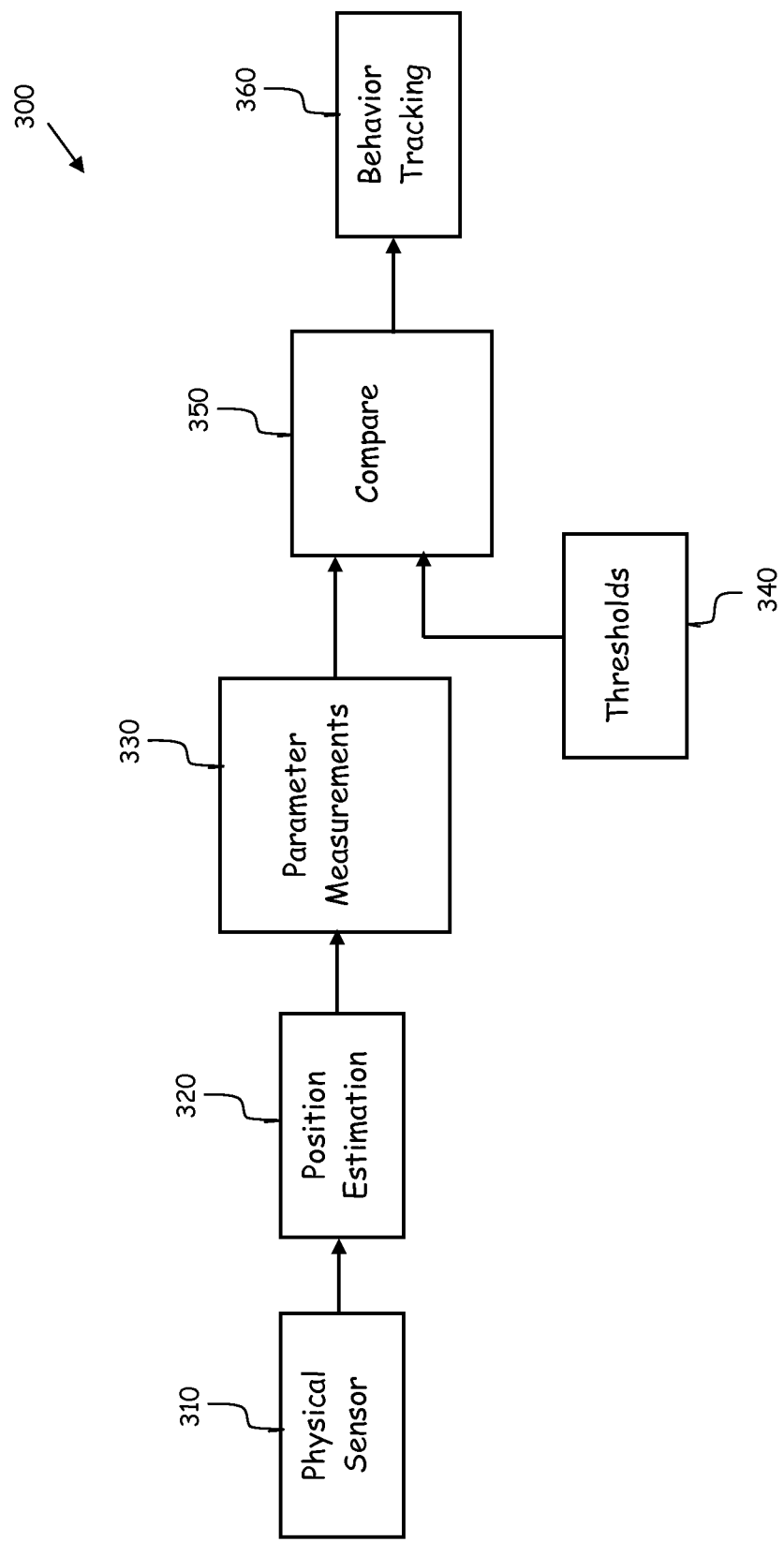
FIG. 3 illustrates a flowchart setting forth a general diagram of a CPR prompting system, according to an embodiment of the invention.

FIG. 3 sets forth a generic overview of applicant's CPR prompting system 300. A first aspect of the system involves acquiring signals from physical sensors at 310. Signals from one or more physical sensors may be used singly or in combination to improve CPR detection, the accuracy of rate and depth measurements, and the latency of those measurements. For example, providing a measurement of the force applied to a CPR puck (or other cardiac assist device), the acceleration of the puck, or the physical response of the patient, allows improved accuracy in the location of the puck to be provided as well as an improved estimation of the effect of the CPR on the patient.

Once the data is acquired, the data is modeled at 320 for estimating the position of the rescuer conducting CPR, or other relevant rescue information. Modeling of the physical system may be done in various ways to better estimate the displacement and the position of the puck in time. Providing a model improves the accuracy of the measurement and allows the current actions of the rescuer to be better understood. The current actions and the immediacy that those actions are recognized provide the basis for providing useful prompts.

Next, measurements are derived at 330 from the model by identifying the critical points in the performance of CPR, and updating the estimate of displacement and of rate at those critical times. Understanding sources of error related to these parameters allows corrections to be made. Further parameters may be derived from the model to improve other aspects of CPR. Absolute position or force may be used to prompt for full release of the compression in some embodiments. The compression, the pumping interval and the release, and the refill interval should be maintained at the same approximate time. CPR performance may be improved by prompting for these parameters as well.

Parameters are then pre-programmed into the system as well as thresholds 340 for a comparison at 350. Alarms are produced upon recognition that the parameters being monitored do not match the ideal. Note that any human performance of a task carries certain variability, which may violate an arbitrary tolerance around the ideal by various amounts and for various intervals. Hysteresis in amplitude, and in time may be employed by the system to produce stable, well defined alarm states, in which both the degree of impact and the useful minimum alarm time can be recognized and specified.

Behavior is tracked, as specified at 360, and prompts are generated to encourage corrections to technique in response to the alarms. Accordingly, embodiments of the present invention relate to a system that can interpret these alarm conditions in a system incorporated with an AED or monitoring device. A simple instantaneous value of rate or depth generally holds little importance as these values are changing continuously. Frequent pauses and time gaps for ventilation complicate prompt system behavior. Embodiments of the present invention provide means to analyze the history of compressions and arrive at consistent, effective corrective prompts, while taking into account certain critical errors in compression that need immediate correction. The trend in the performance history, the variability and change in variability, and the relative importance of different errors are taken into consideration, as well as the past response to prompted corrections.

The effectiveness of accurate and timely corrective prompts for badly performed CPR compressions depends on an intelligent prompting algorithm. The Prompt Engine is the algorithm providing timely and effective corrective prompts, whenever the first responder fails to deliver appropriate compressions measured in terms of rate and depth. Rate is measured in compressions per minute and depth is measured in inches. Also, situations where the first responder does not deploy the CPR sensor correctly or if the sensor readings are within an error zone, special prompts can be issued to enable the first responder to provide proper CPR compressions.

Figure 4:
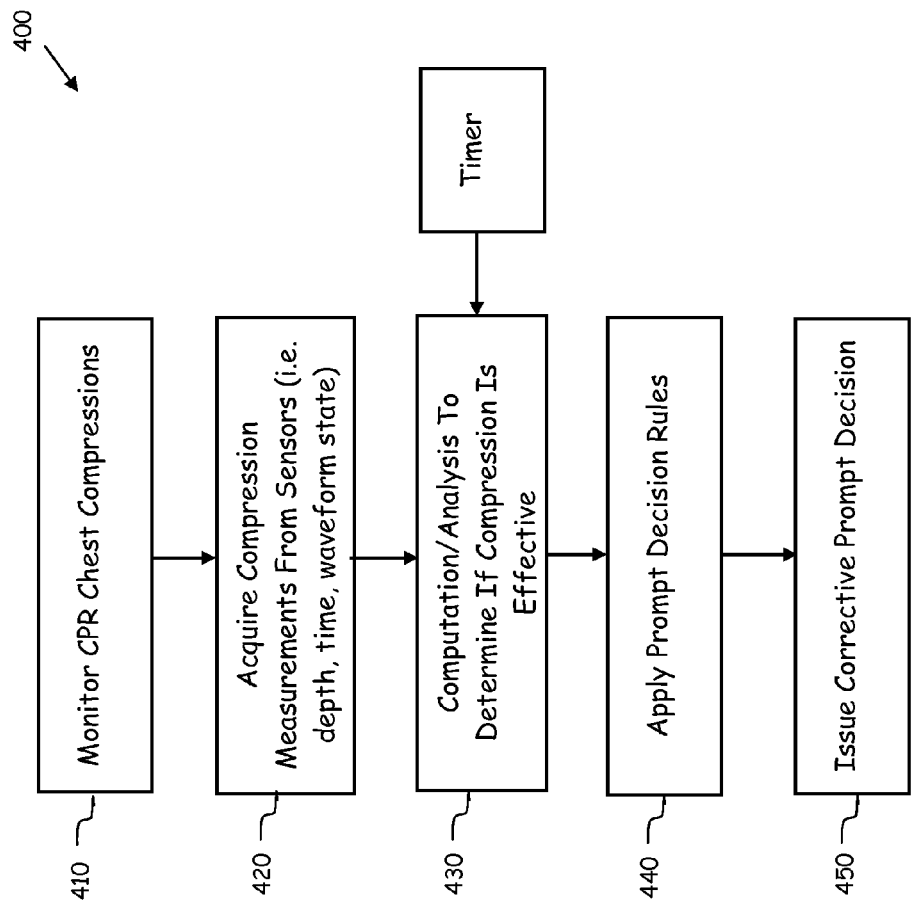
FIG. 4 illustrates generally a flow diagram of a corrective prompting system for chest compressions according to an embodiment of the invention.

A related general flow diagram of a method for a corrective prompting system 400 for producing proper chest compressions can be seen in FIG. 4. The first step 410 is to perform and monitor CPR chest compressions on a cardiac arrest victim. Next, at step 420 sensors from the AED or CPR monitoring device acquire compression measurement data (i.e. depth, time, waveform state). Computation and analysis of data is conducted at 430 according to Applicant's system to determine if the compressions are effective. This data is computed with relevant timing information related to the data. Next, decision rules are applied at 440 to determine if a correction to the current CPR being performed is necessary. Finally, a corrective prompt decision is issued audibly and/or visually if deemed appropriate at 450.

In general, one significant advantage of the various embodiments of the methodology of the present invention from some other past CPR monitoring and data analysis techniques results from use of non-parametric statistics rather than parametric statistics.

Parametric statistics are defined with respect to representation of events within the context of normal distribution and are entirely defined in terms of means and variances. Parametric statistics is a branch of statistics that assumes that data have come from a type of probability distribution and makes inferences about the parameters of the distribution. In general, most well-known elementary statistical methods are parametric.

Non-parametric techniques in statistics do not rely on data belonging to any particular distribution. In other words, they are distribution free methods. Statistics based on the ranks of observations play a major role in non-parametric approaches.

In the current situation in which appropriate detection and setting alarm conditions for proper CPR compressions is desired, a set of compression depths and intervals along with their measurement errors do not satisfy an exact parameterized distribution. Counting tends to be more natural than the actual values of depths and intervals measured once or more during a compression cycle. By counting and ranking the amplitudes of depths and intervals of compressions, a more natural prompt system is made possible.

In embodiments of the present invention, the measurement section is designed to provide M depth measurements and interval measurements in each cycle and in N cycles of compressions, N*M measurements are available. Ranking the values of depth and interval measurements help in creating a histogram of depth and compression rate profile.

Unlike past approaches, embodiments of the invention generally are directed to non-parametric measures for time series analysis. Actual values of the compression depths and rates are not taken for decision making in this invention. An initial expected histogram of the last 4*N measurements from N cycles is generated based on Medical director choice(s) or as per pre-selected American Heart Association (AHA) configurations. Factors influencing a particular expected histogram/probabilistic pattern for depth variations include: (a) Choices of Lower and Higher Thresholds for depth of compression; (b) Proximity of a particular compression cycle to the prompt decision time; (c) Tolerances recommended by emergency care physicians or medical directors; (d) Differential machine performance and errors at lower and higher thresholds; and (e) Patient size and obesity as seen from range of compression depths measured in initial few compressions.

A few samples of possible histogram variations for particular values of Lower Depth Threshold ($D_L$) 502 and Higher Depth Threshold ($D_H$) 504 are shown in FIGS. 5A, 5B, and 5C. In FIG. 5A, a hard threshold is provided for lower and upper limits in the histogram. In FIG. 5B, a tolerance is introduced by additional $D_{L1}$ and $D_{H2}$ values, respectively 506 and 508, and is symmetrical and the same on both upper and lower limits. In FIG. 5C, a nonsymmetrical tolerance is introduced and is different on upper and lower limits.

A histogram represents the probability distribution of a set of values or a time series of values as in the present case. In present invention, bins are adjustable as shown in FIGS. 5A, 5B, and 5C. Amplitudes of histogram are proportional and the total area under the histogram is equal to 1. In other words, if all the measurements are within prescribed limits, area outside is zero. As the measurements happen outside the prescribed limits, area inside the limits decreases and areas outside increase.

Information Theory is a branch of applied mathematics and electrical engineering involving the quantification of information. Such quantification is useful in classification of information and in present invention being used in prompt systems to classify if the chest compression related information indicates a need for a corrective prompt. Information content or entropy, H, of a discrete random variable X is a measure of the amount of uncertainty associated with the value of X.

The definition of Entropy is given below:

$$H(X) = -\sum_{x \in X} p(x) \log p(x)$$

where p(x) probability density function of a result, or a measurement value (of depth or rate) in the present invention. X is the set of all possible results.

In embodiments of the present invention, some assumptions are made about probability density function of an expected set of good compressions, based on user and pre-defined choices as suggested in previous section.

In embodiments of the present invention, information content I(X) is just considered a function of p(x). In other words:

$$I(X) = f(p(x))$$

In actual implementation, this function can be a mapping dictated by choice of lower and higher depth or rate thresholds, weighting based on proximity in time, severity of correction needed and possible errors in measurement.

Figure 6A:
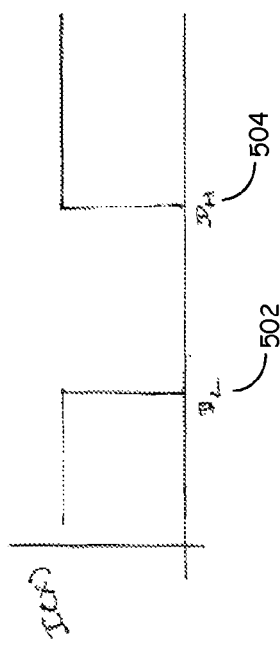
FIGS. 6A-C illustrates generally Information Content I(X) mapped from the corresponding probability density functions in FIGS. 5A-C, according to embodiments of the invention.
Figure 6B:
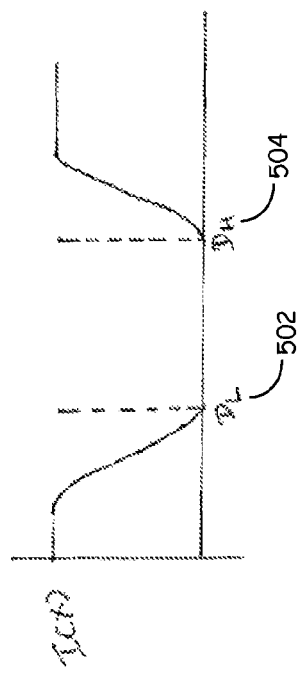
Figure 6C:
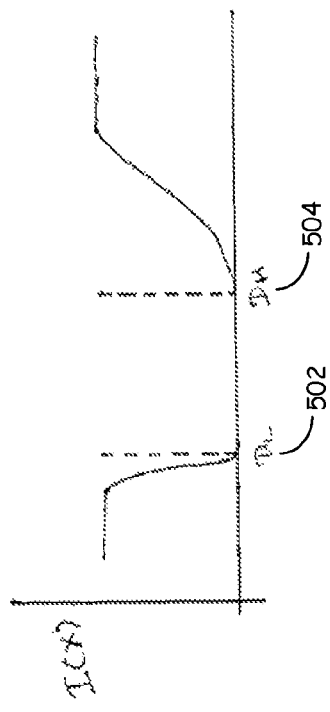

FIGS. 6A, 6B, and 6C indicate the Information Content mapped from the corresponding probability density functions (or) histogram shown in FIGS. 5A, 5B, and 5C.

Any decision making and feedback involving CPR feedback systems involve mainly a collection of a last few samples of depth and rate and utilize a weighted average or auto-regressive moving average (ARMA) of the last few samples of depth and rate. Such approaches suffer from a number of disadvantages, including: the delayed alarm or prompt reaction times due to weighted averaging scheme; the prompt system is completely bound by the ARMA model and cannot react appropriately to huge variations beyond the normal range; one or two outliers can dictate the prompting system behavior; and the assumption of normal distribution of rates and depths may not always be true.

In such cases, decision making systems have been found to be better with non-parametric and information-theoretic approaches. Non-parametric and Information-Theoretic approaches become even more useful, when considering low frequency of computations happening in CPR feedback systems. As prompts happen only once at N seconds, there is no need to compute non-parametric statistics more frequently. Even when the need for corrective prompts is very low, the alarm conditions are computed only twice per second.

Figure 7:
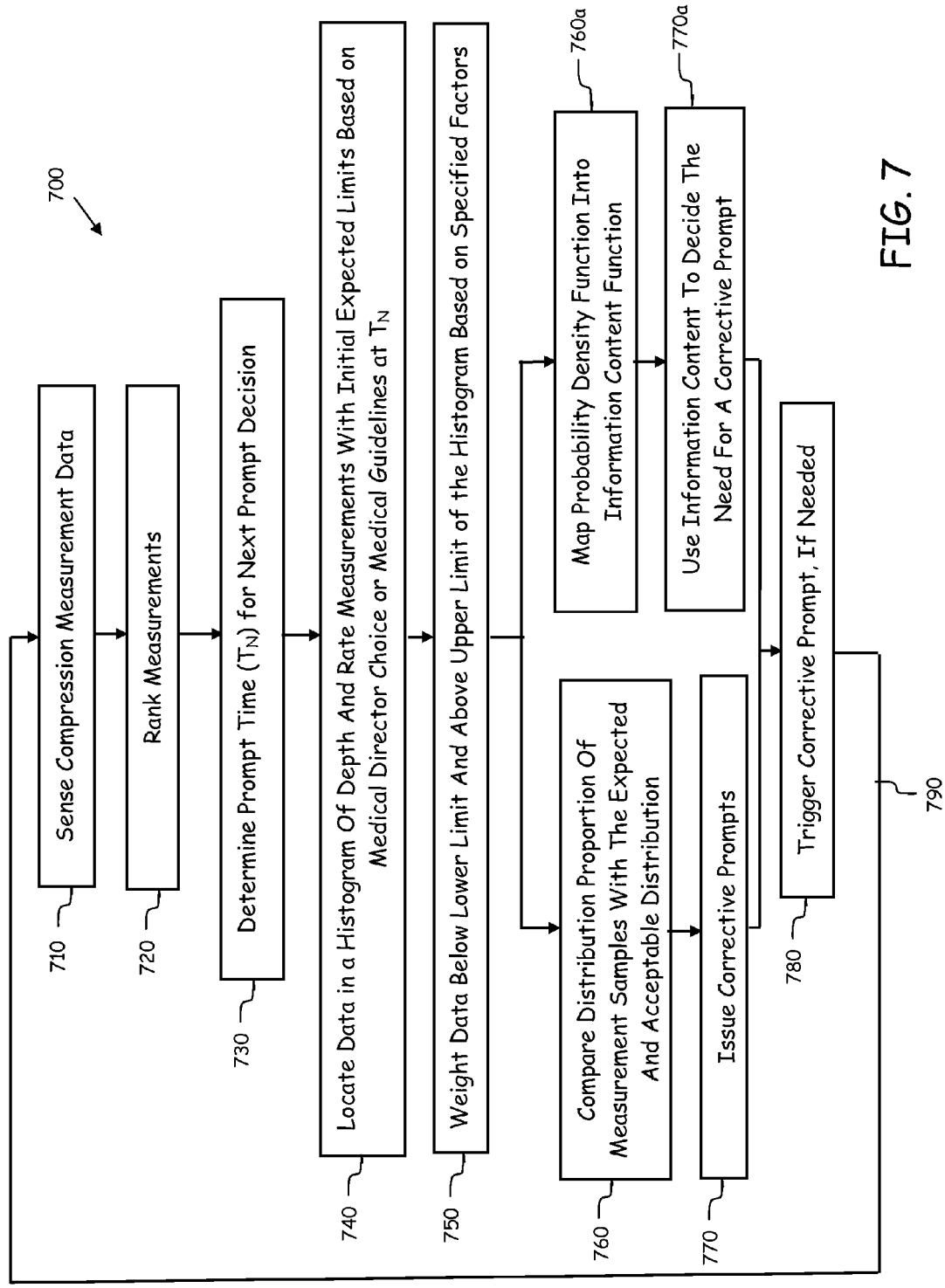
FIG. 7 illustrates generally a flowchart of a generalized embodiment of the analysis and decision-making steps of the CPR feedback system, according to an embodiment of the invention.

FIG. 7 depicts a generalized disclosure of an embodiment of a method of operation of an Information-Theoretic approach to corrective prompting recommendations. The operational method 700, discloses first sensing compression measurement data at 710. Specifically, a measurement system measures and sends the depth or a parameter proportional to depth, time of measurement, and state of measurement in following format: {time(sec), time(sample_count), depth, state}. Once the data is obtained, steps involving a control system including a microprocessor programmed to automatically run an analysis of the compression data and store the results in a memory assessment within the control system occur.

At step 720 the prompt system ranks the measurements as they arrive. Ranking of measurements may take on various forms depending upon the particular embodiment of the invention. In some embodiments, measurements are ranked based upon the depth of compressions being administered. In some embodiments, depth is generally measured from the rank the absolute values of the depth of compressions administered. Some embodiments rank how hard or forcefully compressions are administered and others provide ranking based on depth measurements for compressions administered as well as the time or location in the respiration cycle that compressions are administered. Embodiments may include ranking compression measurement data based on one or more of: compression depth; absolute value of compression depth; force of compressions; when in the respiration cycle compressions are administered; a statistical analysis of any one or more of these values relative to either a norm (e.g. standard deviation), or a predetermined value; or any combination of the foregoing ranking criteria or variations thereof. In various embodiments, ranking may be in either ascending or descending order.

At 730, prompt time, $T_N$, is determined by previous prompt time $T_p$ and intervals between prompts (T) and emergency of the correction needed. Next, at 740 data is located in a histogram of depth and rate measurements at prompt time, $T_N$ that are applied to an initial expected histogram with limits based on medical director choice or guidelines of a medical association. Histogram intervals are divided into three sections: one between lower and upper limits for rate and depth measurements (from user-choice and AHA guidelines) (Section 1); a section below lower limit (Section 2); and a section above upper limit (Section 3). Next, at 750, data observations falling in Sections 2 and 3 are further weighted by four factors: proximity in time (weights decreasing with time; nearer events having more weights); possible asymmetry in measurement errors; any tolerances specified by first-responder or medical supervisors (such as giving more priority to insufficient compression depth compared to more than sufficient compressions); and any outliers like pauses and huge measurements or user-related errors.

At 760 the proportion of distribution of measurement samples in three sections computed in 750 is compared with expected and acceptable distribution. At 770, when the proportion indicates a higher probability of insufficient compressions or too deep or too fast compressions, appropriate corrective prompts are issued.

As an alternative to steps 760 and 770, the system may instead first derive information content of the measurements in the decision window using the equation discussed above at 760a. In some implementation embodiments, probability density function is mapped into information content function using a table or similar techniques. Next, at 770a, information content may be used to decide the need for a particular corrective prompt.

Figure 8:
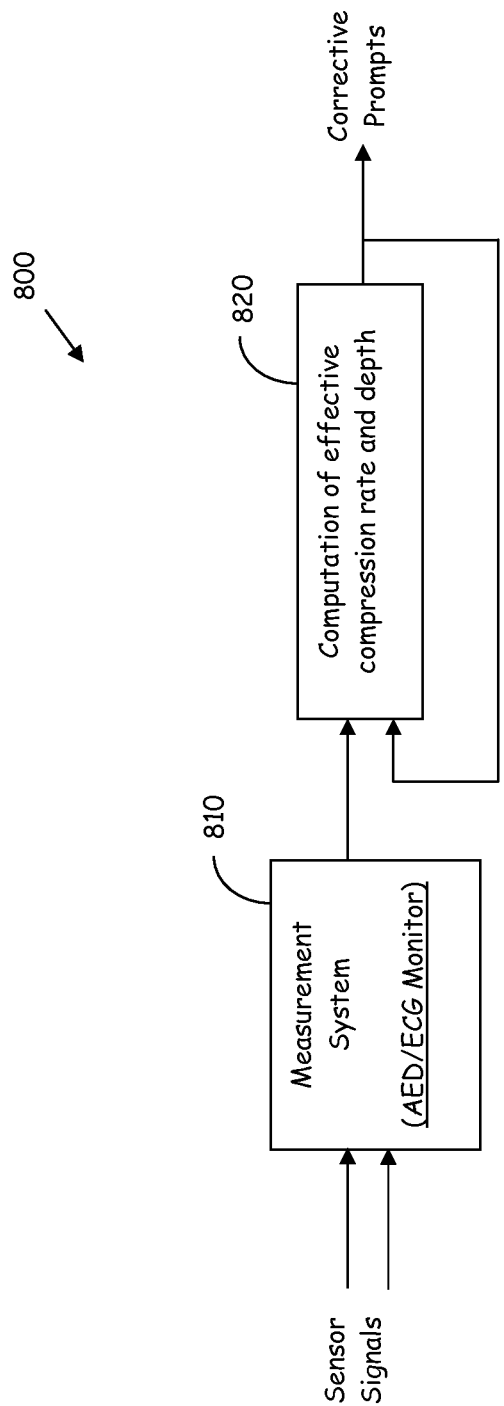
FIG. 8 illustrates generally a flowchart of a measurement and prompt system for corrective prompting, according to an embodiment of the invention.

Next, at 780, information content may be used to enable a trigger of corrective prompting even with one measurement that shows a need for immediate correction. Finally, at 790, if no corrective prompts are required at $T_N$, the computations are repeated after 0.5 seconds ($T_N$+0.5) and the earlier steps are repeated. (Depending on the prompt system design, the computations can be repeated more or less frequently. Specifically, in some embodiments the computations are repeated after periods of more than 0.5 seconds and in some embodiments the computations are repeated after periods of less than 0.5 seconds.) Otherwise, one should wait for a minimum time between prompts (T) before repeating the earlier steps. FIG. 8 provides an embodiment of a measurement system and prompt system 800. The measurement system and prompt system shown here may be in same system or two independent systems connected by communications channel.

An AED can acquire a signal representative of CPR compressions and can directly or indirectly measure the depth and rates of compression. An AED also records a patient's electrocardiogram (ECG) signals after the placement of electrode pads. These components are represented by measurement system 810 in FIG. 8. Embodiments of the present invention describe a system that measures signals representative of circulation and compressions during CPR. Such signals can be measured with piezo-electric, resistive, capacitive, magnetic, optical and/or acoustic transducers.

During CPR chest compressions, the frequency of these variations can illustrate the rate of compressions and a careful calibration can provide an adequacy of compressions and can provide actual compression depth in some cases of measuring sensors like accelerometer, or a force sensor. A component representing the computation and prompt system 820 is shown in FIG. 8 as well.

Figure 9A:
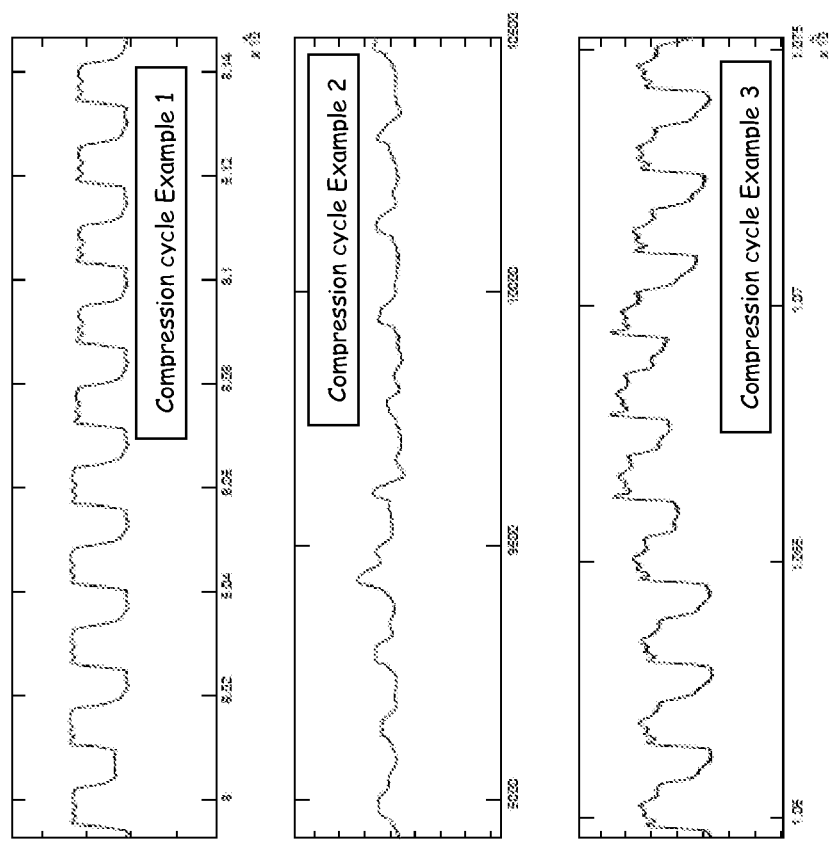
FIG. 9A-C illustrate generally examples of CPR compression cycle waveforms from a sensor, according to embodiments of the invention.
Figure 9B:
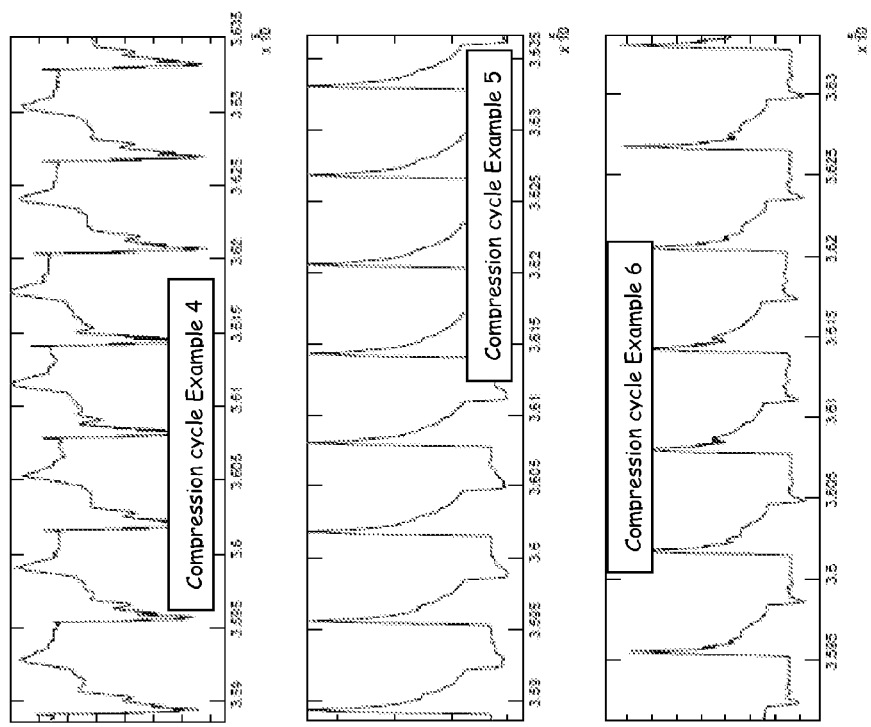
Figure 9C:
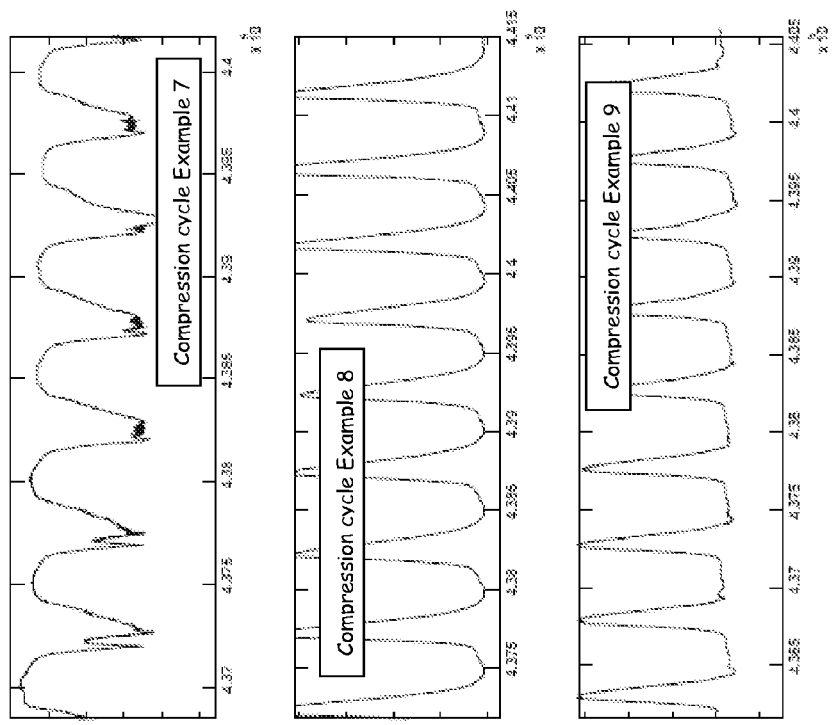

A few typical variations of CPR compression cycle waveforms from a sensor (non-calibrated) are shown in FIGS. 9A-C. The waveform shapes, amplitudes and signs are generally dependent on the nature of the recording sensors, patient body size and electromechanical characteristics, physics behind signal acquisition, any pre-processing involved and the nature of compressions or natural circulation happening at the point of time.

Each one of the waveforms need to be calibrated and rates and depth (if possible) can be measured. Some of these waveforms are more indicative of blood flow and circulation than actual depth of compressions. However, all of them maintain information about the rate of chest compressions.

FIGS. 9A and 9B provide a number of examples of CPR compression cycle waveforms of non-calibrated measurements from a sensor. FIG. 9C provides a number of examples of CPR compression cycle waveforms representing the diversity of measurement waveform characteristics.

In embodiments of the present invention there are a number of inputs required in order for the prompt system to operate. First, at every sample, a structure with the details [sample_count; time(sec); depth; state] is passed on from measurement module to prompt engine. Next, the original sensor input arrives at prompt engine at a pre-fixed sampling rate or whenever a new measurement of depth is made in a measurement cycle. "Depth" information can be instantaneous, continuous amplitudes at a particular sampling rate of Fs Hz or at discrete times only when measurements are made at states corresponding to complete push to bottom and at complete release to top. "State" can be one of the four states: PUSH, BOTTOM, RELEASE and TOP. A compression cycle can be defined as per the signal characteristics revealed by a particular depth sensor.

Accordingly, various embodiments of the prompt system may send one of the following outputs for every sample: DO_NOTHING; PROMPT_PRESS; PROMPT_PRESS_HARDER; PROMPT_PRESS_SOFTER; PROMPT_PRESS_FASTER; PROMPT_PRESS_SLOWER. User options include: PROMPT_BOTH (prompts for both depth and rate corrections); PROMPT_DEPTH_ONLY (prompts for depth only); and PROMPT_RATE_ONLY (prompts for rate only). User choices may include: PROMPT_TIME; PRIORITY; and PATIENT ADAPTIVE vs. FIXED.

Updates in depth ('adepth') happen at all four states mentioned above and are stored in a rolling buffer that can accommodate M previous compressions (4*M measurements). Updates in intervals and rates can happen in above states and stored in a rolling buffer that can accommodate M previous compression cycles (4*M measurements).

In embodiments of the present invention, when a corrective prompt decision is made at $t=T_N$, each incoming measurement is located and weighted in histogram based on its value, upper and lower limits selected by system or medical director, proximity in time to decision point, possible errors in measurement, tolerances specified, and measurement being a outlier.

For example, a measurement inside valid limits of rate will have a weight of 1 and those outside the valid limits will have a weight that is a function of above factors. In other words, a measurement of rate falling between $R_L$ and $R_H$ will have a count of 1 in histogram computation and a measurement of rate just above $R_H$ will have a count of 1.1 and a measurement further away from $R_H$ will have a count of 1.2 and so on. An outlier further away from prescribed limits will have more impact on corrective prompting compared to one that is closer to prescribed limits. In another model, presence of larger pauses can indicate the cessation of CPR activity and continuous computation of effective CPR rate can be stopped. In other words, all the weights can be reset to 0.

Depth decision rules are similar to rate decision rules, described above. In another model, presence of larger pauses can indicate the cessation of CPR activity and continuous computation of effective CPR depth can be stopped. In other words, all the weights can be reset to 0. In both rate and depth decision systems, proportion of areas inside the bins between upper and lower limits, area above the upper limit and area below the lower limits dictate the corrective prompting schemes.

The four corrective prompts that are assumed are as follows: {Press Harder, Press Softer, Press Faster, Press Slower}. Additional standard prompt can be {Press Harder and Release Fully}, in case of unknown mistakes detected in measurement process/algorithm or in the first responder/sensor interactions. Every N seconds, a corrective prompt is generated. Depth related prompts alternate with rate related prompts, when PROMPT_BOTH is chosen. For example: depth related prompts at t=T sec, 3T sec, 5T sec, and so on; and rate related prompts at t=2T sec, 4T sec, 6T sec, and so on. Corrective rate prompts are given for rates outside $[R_L, R_H]$ range. Corrective depth prompts are given for depths outside $[D_L, D_H]$ range. When no correction needed, no corrective prompts are given. Under no compression condition (Pauses) during CPR, default prompts are: Press Harder and Press Softer.

Pauses are identified by any time above $T_O$ sec, from previous PUSH state; in other words, if no new compressions detected within $T_0$=1.2 seconds, following updates take place in interval and depth measurements: {0.0, 0.0}, every $T_0$ seconds.

Various embodiments are made possible by the disclosed system. In a first embodiment, a Fixed Time, Alternating Depth/Rate Correction System is provided. In this model time between prompts is fixed and the first prompt is towards depth correction and is followed by rate corrective prompt and this sequence is repeated until the end of a cycle of CPR compressions. At times T, 3T, . . . , check for corrective prompt alarm conditions for depth with limits <$D_L, D_H$>; if outside the limits, issue a corrective prompt alarm or flag. Else, perform no action. At times 2T, 4T, . . . , check for corrective prompt alarm conditions for rate with limits <$R_L, R_H$>; if outside the limits, issue a corrective prompt alarm or flag. Else, perform no action. Maximum frequency of prompting in this model is limited by time between the prompts. Average frequency of prompting is decided by the need for depth and rate prompts required in a CPR session.

In a second embodiment, a Fixed Time, Depth Only Correction System is provided. This embodiment is a variation of the first embodiment, however, the frequency of depth prompt is increased by a factor of 2. At times T, 2T, 3T, . . . , check for corrective prompt alarm conditions for depth with limits <$D_L, D_H$>; if outside the limits, issue a corrective prompt alarm or flag. Else, perform no action.

In a third embodiment, a Fixed Time, Rate Only Correction System is provided. This embodiment is a variation of the first embodiment, however, the frequency of rate prompt is increased by a factor of 2. At times T, 2T, 3T, . . . , check for corrective prompt alarm conditions for rate with limits <$R_L, R_H$>; if outside the limits, issue a corrective prompt alarm or flag. Else, perform no action.

In a fourth embodiment, a Fixed Time, Depth followed by Rate in Priority Correction System is provided. In this embodiment, the time between corrective prompts is kept constant. If no depth related corrective prompt is needed, then only a rate related prompt is given out, if needed.

In a fifth embodiment, a Variable Time, Depth followed by Rate in Priority Correction System is provided. In this embodiment, the time between adjacent corrective prompts is variable, thereby enabling a minimum effective latency. Minimum time between corrective prompts is fixed ($T_{Min}$) and a corrective prompt can happen at any time point ($T_{Min}$+ $nT_D$). Usually, $T_{Min} \gg T_D$ and n=0, 1, 2, . . . . Always the prompt system looks for any need for depth-related corrective prompt and if there is no correction needed for depth, then it looks for rate-related corrective prompt.

In a sixth embodiment, a Variable Time, Variable Adaptive Threshold Based System is provided. This embodiment is similar to the fifth embodiment, however, a major difference is in the adaptive thresholding based on patient profile. Based on effective depth computations in the first few seconds, prompting system will adjust for bulkier patients. Similarly, for each responder, the system can adapt based on initial few seconds of compressions. This scheme of operation is applicable to all the earlier models.

In a seventh embodiment, alarm conditions based on measurement errors and CPR quality is provided. In the event of sudden failure of sensor systems and/or poor quality CPR being delivered in terms of ill-defined "PRESS-RELEASE" cycles, In an eighth embodiment, Multiple Sensor Sources for Depth/Rate Correction systems are provided. In the absence of an exact sensor being not used for depth measurement, one or more other sensors can provide a depth alone (or) rate alone corrective prompting. In a situation below, a sensor attached to the first-responder's hand can provide a measure of the hand movement and can indicate the depth and the rate of hand movements, provided they touch the secondary sensor on patient chest.

In a ninth embodiment, a Machine CPR adaptive decision rule is provided. In case of CPR performed by machines, once the Prompt system learns the exactness of compressions in terms of rate and depth, the prompt system keeps silent mode and observes for only breaks or pauses at unexpected times.

In a tenth embodiment, a Learning device and Manikin decision rule is provided. In this embodiment, an adaptive device that is meant for demonstration is visualized. The user can choose possible embodiments in a PC based system and start doing compressions on a manikin. A correction factor corresponding to the use of manikin will be applied and prompt system will provide appropriate corrective prompts.

While these ten embodiments are separately set forth above, other embodiments may include a combination of two or more of the embodiments described above or portions thereof.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. An automated external defibrillator (AED) having a corrective cardio-pulmonary resuscitation (CPR) prompting system, comprising:
    a sensor that provides compression measurement data representative of CPR chest compressions;
    a control system including a microprocessor programmed to automatically run a non-parametric, Information-Theoretic analysis of the compression measurement data and store results in a memory within the control system, the analysis including:
        ranking provided compression measurement data as the compression measurement data is provided from the sensor;
        determining a prompt time $T_N$ in the future for review;
        locating the compression measurement data that has been ranked at $T_N$ in an initial expected histogram creating a histogram of depth and rate aspects of the compression data measurements with upper and lower limits, that divides the intervals of the histogram into a plurality of sections;
        weighting the compression measurement data located in the plurality of sections of the histogram based on a plurality of factors;
        deriving information content of the compression measurement data, after weighting the compression measurement data, by mapping a probability density function into an information content function; and
        determining if one of a plurality of corrective prompts are necessary based on the information content of the compression measurement data that has been derived; and
    a prompting device that provides corrective CPR instructions corresponding to the one of the plurality of corrective prompts that are determined by the control system to be necessary.

2. The automated external defibrillator of claim 1, wherein a plurality of sensors provide the compression measurement data.

3. The automated external defibrillator of claim 1, wherein the sensor is part of a cardiac assist device.

4. The automated external defibrillator of claim 1, wherein the plurality of factors include proximity in time, asymmetry in measurement errors, tolerances specified by first-responders, and outlier data.

5. The automated external defibrillator of claim 1, wherein the intervals of the histogram are divided into three sections.

6. The automated external defibrillator of claim 1, further including sensors adapted to provide ECG data.

7. The automated external defibrillator of claim 1, wherein the sensor is selected from the set consisting of: a piezoelectric sensor, a pressure sensor, an accelerometer, a force sensor, an ultrasonic sensor, an infrared sensor, or any combination thereof.

8. The automated external defibrillator of claim 1, wherein ranking provided compression measurement data includes ranking depth measurements of compressions administered.

9. The automated external defibrillator of claim 1, wherein ranking provided compression measurement data includes ranking absolute values for depth measurements of compressions administered.

10. The automated external defibrillator of claim 1, wherein ranking provided compression measurement data includes ranking how forcefully compressions are administered.

11. The automated external defibrillator of claim 1, wherein ranking provided compression measurement data includes ranking the depth measurements of compressions administered and when in the respiration cycle compressions are administered.

12. The automated external defibrillator of claim 1, wherein ranking provided compression measurement data is based on one or more of: compression depth; absolute value of compression depth; force of compressions; and when in the respiration cycle compressions are administered.

13. The automated external defibrillator of claim 1, wherein ranking the compression measurement data is based on one or more of: compression depth; absolute value of compression depth; force of compressions; and when in the respiration cycle compressions are administered.

* * * * *